US010149923B2

(12) United States Patent
Carter

(10) Patent No.: US 10,149,923 B2
(45) Date of Patent: Dec. 11, 2018

(54) IMPLANTS FOR SOFT AND HARD TISSUE REGENERATION

(71) Applicant: Tepha, Inc., Lexington, MA (US)

(72) Inventor: Andrew J. Carter, Stow, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 14/151,561

(22) Filed: Jan. 9, 2014

(65) Prior Publication Data
US 2014/0200667 A1    Jul. 17, 2014

Related U.S. Application Data

(60) Provisional application No. 61/752,947, filed on Jan. 15, 2013.

(51) Int. Cl.
*A61L 27/58* (2006.01)
*A61L 27/46* (2006.01)
(Continued)

(52) U.S. Cl.
CPC .............. *A61L 27/58* (2013.01); *A61F 2/08* (2013.01); *A61F 2/28* (2013.01); *A61L 27/18* (2013.01);
(Continued)

(58) Field of Classification Search
CPC ...... A61F 2002/2839; A61F 2002/2835; A61F 2/0063; A61F 2002/0068; A61F 2/08
See application file for complete search history.

(56) References Cited

U.S. PATENT DOCUMENTS 4,224,946 A * 9/1980 Kaplan ............... A61L 17/04
606/231
4,279,249 A   7/1981 Vert
(Continued)

FOREIGN PATENT DOCUMENTS

DE    3810803    10/1988
EP    0277678    8/1988
(Continued)

OTHER PUBLICATIONS

Hori, et al., "Chemical synthesis of high molecular weight poly(3-hydroxybutyrate-co-4-hydroxybutyrate", Polymer, 36:4703-5 (1995).
(Continued)

*Primary Examiner* — Thomas Sweet
(74) *Attorney, Agent, or Firm* — Pabst Patent Group LLP

(57) ABSTRACT

Implants for osteo and osteochondral repair have been developed. These implants include a series of channels between the upper and lower surfaces of the implants, such that when implanted the lower surfaces are situated in an area rich in bone marrow and the channels provide a means for the bone marrow to migrate through the implant. Preferably the implants are made from resorbable polymer fibers, preferably arranged in braids that are knitted or woven together such that the braids are substantially parallel with each other. The implants may be rolled into a bundle of braids with the axis of the braids substantially parallel to the axis of the bundle, to provide channels along the axis of the bundle. A preferred embodiment includes P4HB fibers braided and knitted into a structure that is coated with a ceramic, preferably physiologic calcium phosphate.

35 Claims, 1 Drawing Sheet

(51) Int. Cl.
  *A61L 27/18* (2006.01)
  *A61L 27/54* (2006.01)
  *A61L 27/56* (2006.01)
  *A61L 27/32* (2006.01)
  *A61F 2/08* (2006.01)
  *A61F 2/28* (2006.01)
  *D04C 1/02* (2006.01)
  *D04B 1/14* (2006.01)

(52) U.S. Cl.
  CPC .............. *A61L 27/32* (2013.01); *A61L 27/46* (2013.01); *A61L 27/54* (2013.01); *A61L 27/56* (2013.01); *D04B 1/14* (2013.01); *D04C 1/02* (2013.01); *A61L 2300/30* (2013.01); *A61L 2300/414* (2013.01); *A61L 2300/606* (2013.01); *A61L 2430/02* (2013.01); *A61L 2430/06* (2013.01); *A61L 2430/10* (2013.01)

(56) References Cited

U.S. PATENT DOCUMENTS

| | | | |
|---|---|---|---|
| 5,306,311 A | 4/1994 | Stone | |
| 5,514,181 A * | 5/1996 | Light et al. | 623/13.18 |
| 5,607,474 A | 3/1997 | Athanasiou | |
| 5,811,272 A | 9/1998 | Snell | |
| 5,977,204 A * | 11/1999 | Boyan et al. | 523/113 |
| 6,245,537 B1 | 6/2001 | Williams | |
| 6,316,262 B1 | 11/2001 | Huisman | |
| 6,323,010 B1 | 11/2001 | Skraly | |
| 6,511,511 B1 | 1/2003 | Slivka | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 6,946,003 B1 * | 9/2005 | Wolowacz | A61F 2/08 623/23.72 |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,641,825 B2 | 1/2010 | Rizk | |
| 7,906,135 B2 | 3/2011 | Williams | |
| 7,943,683 B2 | 5/2011 | Rizk | |
| 8,016,883 B2 | 9/2011 | Coleman | |
| 8,034,270 B2 | 10/2011 | Martin | |
| 8,039,237 B2 | 10/2011 | Martin | |
| 8,663,332 B1 * | 3/2014 | To | A61F 2/442 623/17.12 |
| 9,364,310 B2 * | 6/2016 | Stopek | A61F 2/0063 |
| 2003/0006534 A1 * | 1/2003 | Taboas et al. | 264/401 |
| 2004/0234576 A1 * | 11/2004 | Martin | A61F 2/0063 424/426 |
| 2004/0267362 A1 * | 12/2004 | Hwang et al. | 623/13.15 |
| 2007/0032805 A1 * | 2/2007 | Therin | A61F 2/0063 606/151 |
| 2007/0061015 A1 | 3/2007 | Jensen | |
| 2007/0265710 A1 * | 11/2007 | Brown | A61F 2/0063 623/23.72 |
| 2007/0297987 A1 * | 12/2007 | Stad | A61B 17/0642 424/9.4 |
| 2007/0299542 A1 * | 12/2007 | Mathisen | A61F 2/0063 623/23.75 |
| 2008/0109070 A1 * | 5/2008 | Wagner et al. | 623/1.41 |
| 2009/0069904 A1 | 3/2009 | Picha | |
| 2009/0287308 A1 * | 11/2009 | Davis | A61F 2/08 623/13.12 |
| 2011/0318402 A1 * | 12/2011 | Ahn | 424/423 |
| 2012/0150204 A1 * | 6/2012 | Mortarino | A61F 2/0063 606/151 |
| 2012/0179176 A1 * | 7/2012 | Wilson | A61F 2/0063 606/151 |
| 2012/0271431 A1 * | 10/2012 | Nies et al. | 623/23.53 |
| 2013/0218253 A1 * | 8/2013 | Kaufmann et al. | 623/1.2 |
| 2013/0267137 A1 * | 10/2013 | Peniston | D04B 21/12 442/50 |
| 2013/0304098 A1 * | 11/2013 | Mortarino | A61F 2/12 606/151 |

FOREIGN PATENT DOCUMENTS

| | | |
|---|---|---|
| EP | 1357953 | 11/2005 |
| WO | 9853768 | 12/1998 |
| WO | 99032536 | 7/1999 |
| WO | 0032749 | 6/2000 |
| WO | 2000056376 | 9/2000 |
| WO | 2009085823 | 7/2009 |
| WO | 2010093333 | 8/2010 |
| WO | 2011159784 | 12/2011 |

OTHER PUBLICATIONS

Houk, et al., "Why delta-valerolactone polymerizes and gamma-butyrolactone does not", J. Org. Chem., 73 (7):2674-8 (2008).

Martin, et al., "Medical Applications of Poly-4-hydroxybutyrate: A Strong Flexible Absorbable Biomaterial", Biochem. Eng. J., 16:97-105 (2003).

Moore, et al., "Chemosynthesis of bioresorbable poly(gamma-butyrolactone) by ring-opening polymerisation: a review", Biomaterials, 26:3771-82 (2005).

Steinbüchel, et al., "Diversity of Bacterial Polyhydroxyalkanoic Acids", FEMS Microbial. Lett., 128:219-28 (1995).

Williams, et al., "Application of PHAs in Medicine and Pharmacy", Polyesters, III:4:91-127 (2002).

\* cited by examiner

FIG. 1A     FIG. 1B
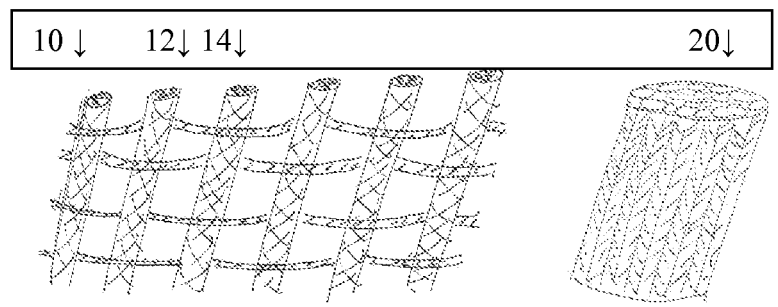
FIG. 2
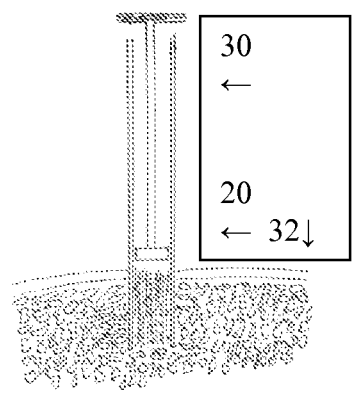

IMPLANTS FOR SOFT AND HARD TISSUE REGENERATION

CROSS-REFERENCE TO RELATED APPLICATIONS

This application claims the benefit of and priority to U.S. Provisional Application No. 61/752,947, filed Jan. 15, 2013.

FIELD OF THE INVENTION

The present invention generally relates to compositions and implants comprising resorbable polymer fibers for the regeneration of tissue. The implants can be used in many types of surgery but are most suited to use in osteo and osteochondral defect repair, as well as ligament and tendon repair.

BACKGROUND OF THE INVENTION

The tissues that compose and support joint surfaces are collectively called osteochondral tissues. The most superficial of these, the articular cartilage, is essential for absorbing shock and maintaining normal joint environment, and, regardless of the cause, degeneration of articular cartilage can result in irreversible osteoarthritis. While this loss of cartilage is the most noticeable affect of osteoarthritis there are also many changes to the underlying bone caused by injury and osteoarthritis. In degenerated joints there is a thickening, or sclerosis of the bone and frequently the formation of bone marrow lesions. Nutrition to these tissues is provided by the bone marrow and disruption of the tissues may also compromise nutrition causing further degeneration.

Debate continues as to the initial event(s) that causes osteoarthritis. Some investigators contend that articular cartilage changes precede subchondral bone changes; while other investigators contend the opposite. It appears that changes in articular cartilage and subchondral tissues are so intertwined that distinguishing a single initiating change in either tissue is difficult. However it is clear that any strategies for repair of cartilage defects or cartilage bone defects must account for changes to the bone.

A number of medical devices have been developed to facilitate the repair of osteo and osteochondral defects. These devices typically comprise cylindrical plugs that can be inserted into holes drilled perpendicular to, and through, the articular cartilage of the defect. The osteochondral plugs are often bi-phasic in design with each phase designed to regenerate either the articular cartilage tissue or the bone by aligning with that tissue in vivo. The devices are generally made from resorbable materials, and often comprise fibers dispersed in a second material.

U.S. Pat. No. 4,279,249 to Vert et al. discloses a non-porous osteosynthesis device made from biodegradable polymers that is reinforced with fibers. U.S. Pat. No. 5,306,311 to Stone et al. discloses a resorbable scaffold for articular cartilage regeneration comprising a porous matrix of randomly, circumferentially or radially oriented fibers such that the matrix has a surface contour substantially the same as natural articular cartilage. Preferably, at least some of the fibers are cross-linked. EP Patent No. 0,277,678 A1 to Leenslag et al. discloses grafts for use in reconstructive surgery that are matrices of organic polymeric materials incorporating degradable fibers having a bi-porous structure with each structure having its own pore size and pore size distribution. EP Patent No. 1,357,953 to Callegaro et al. discloses grafts for the repair of osteochondral defects wherein the grafts are constituted by a three-dimensional matrix of hyaluronic acid derivatives with a structure containing empty spaces; a porous, three-dimensional matrix constituted by a ceramic material; optionally containing pharmacologically or biologically active ingredients. U.S. Pat. No. 5,607,474 to Athanasiou et al. discloses multi-phase bioerodible implants for osteo and osteochondral defect repair. These implants include a first bioerodible polymeric material bonded to a second bioerodible polymeric material with each material having different mechanical properties. These biphasic porous implants are implanted such that the first material resides substantially within the bone of an osteochondral defect, and the second material resides substantially within the cartilage. Each material is selected and formed to permit tissue ingrowth in order to allow regeneration of bone and cartilage. U.S. Pat. No. 6,511,511 to Slivka et al. discloses fiber-reinforced polymeric implants that can be used for osteo and osteochondral repair, wherein the chopped fibers are aligned inside biodegradable porous matrices and the ratio of the volume of fibers to the biodegradable polymeric material is between 0.05 and about 0.5.

In order to further improve the repair of osteochondral defects, it is desirable to identify an implant that can allow good communication between the base of the defect (in the bone), and the cartilage surface. Ideally, the implant would permit cells that populate the bone marrow to migrate throughout the defect resulting in improved regeneration of both the bone and the cartilage. Furthermore, it is desirable for the repair to be deep enough to reach through the diseased and sclerotic bone tissue to the bone marrow, since nutrition is derived from the bone marrow deep below the cartilage surface.

It is therefore an object of the present invention to provide implants that will facilitate the regeneration of the tissue in osteo and osteochondral defects, and in ligament and tendon injuries.

It is further object of the invention to provide implants comprising a means such that when implanted the lower surfaces are situated in an area rich in bone marrow and the bone marrow can migrate through the implant.

It is still another object of the invention to provide methods for manufacturing biocompatible implants comprising fibers or braids coated with bioceramic, and methods of manufacture, to enhance osteointegration.

It is yet another object of the invention to provide methods for implanting the implants.

SUMMARY OF THE INVENTION

Implants for osteo and osteochondral repair have been developed. These implants comprise a series of channels between the upper and lower surfaces of the implants, such that when implanted the lower surfaces are situated in an area rich in bone marrow and the channels provide a means for the bone marrow to migrate through the implant. Preferably the implants are made from resorbable polymer fibers. These fibers are preferably arranged in braids that are knitted or woven together such that the braids are substantially parallel with each other. The implants may be rolled into a bundle of braids with the axis of the braids substantially parallel to the axis of the bundle so as to provide channels along the axis of the bundle. Alternatively the device may be used to wrap around an injured tendon or ligament. A preferred embodiment comprises P4HB fibers braided and knitted into a structure that is coated with a ceramic, preferably physiologic calcium phosphate. The implant may be injected with additional therapeutic or diagnostic materials such as hyaluronic acid to facilitate clot formation and healing.

In a preferred embodiment, the implant is rolled and delivered through a tubular inserted introduced into the defect to be repaired.

BRIEF DESCRIPTION OF THE DRAWINGS

FIGS. 1A and 1B are a prospective view of the implant structure as produced (1A) and rolled up (1B) to form an implant suitable for treating osteo and osteochondral injuries.

FIG. 2 is a prospective view of an introducer used to place the implant in an osteochondral defect.

DETAILED DESCRIPTION OF THE INVENTION

Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Lexington, Mass.).

"Copolymers of poly-4-hydroxybutyrate" as generally used herein means any polymer comprising 4-hydroxybutyrate with one or more different hydroxy acid units.

"Bioactive agent" is used herein to refer to therapeutic, prophylactic, or diagnostic agents. It includes physiologically or pharmacologically active substances that act locally or systemically in the body. A biologically active agent is a substance used for, for example, the treatment, prevention, diagnosis, cure, or mitigation of disease or disorder, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, sugars and polysaccharides, nucleotides and oligonucleotides including aptamers, siRNA, and combinations thereof.

"Bioceramic" means a ceramic suitable for use or replacement in the human body.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer comprised of two or more different monomers.

"Ceramic" means an inorganic, nonmetallic solid prepared by the action of heat and subsequent cooling.

"Molecular weight" as used herein, unless otherwise specified, refers to the weight average molecular weight (Mw), not the number average molecular weight (Mn), and is measured by GPC relative to polystyrene.

"Resorbable" as generally used herein means the material is broken down in the body and eventually eliminated from the body.

"Resorbable bioceramic" means a bioceramic that is used to replace or repair damaged tissue in the body, and is eventually resorbed such that the host replaces the implant. Examples include tricalcium phosphate (TCP), calcium sulfate, calcium carbonate, and other calcium phosphate salt-based bioceramics. Used herein the term will also encompass bioactive glasses composed of $SiO_2$, $Na_2O$, $CaO$ and $P_2O_5$ in specific proportions.

I. Implants

A. Channeled Polymeric Implants

Implants comprising a series of channels between the upper and lower surfaces of the implants are provided to improve the repair of osteo and osteochondral defects. These implants provide improved communication between the base of the defect, and the cartilage surface, and permit cells that populate the bone marrow to migrate throughout the defect resulting in improved regeneration. The implants are designed to reach through the diseased and sclerotic bone tissue in order for the regenerating tissue to obtain nutrition from the bone marrow deep below the cartilage surface. Preferably, the implants are cylindrical, and are implanted in holes drilled perpendicular to, and through, the articular cartilage. In order to minimize thermal necrosis of the wound margins, the holes should preferably be drilled with a sharp and well irrigated drill.

In one embodiment, the implant comprises a series of channels between the upper and lower surfaces of the implants such that when implanted the lower surfaces are situated in an area rich in bone marrow and the channels provide a means for the bone marrow to migrate through the implant. Preferably the channels run continuously from the upper to the lower surfaces of the implants. In a preferred embodiment, the channels of the implants are formed by aligning a series of fibers, braids or other textile structures substantially parallel to each other. Such structures may contain hollow cores. In an even more preferred embodiment, the channels are formed using resorbable materials, including resorbable polymers.

In a preferred embodiment, the porosity of the implant is between 25 and 70% by weight, and the volume of the implant occupied by the materials is from 30 to 75%. In a particularly preferred embodiment, the porosity of the implant is between 35 and 60%.

In an even more preferred embodiment, the implant comprises a number of braided resorbable polymer fibers oriented substantially parallel to each other. Upon implantation, the implant is placed such that the braids are oriented substantially parallel to the axis of the defect. In one embodiment, shown in FIGS. 1A and 1B, the braids formed from fibers 12 and 14 are preferably lightly woven or knitted together to provide a fabric mat 10, which is then rolled up to form a cylindrical implant 20 to facilitate implantation.

The orientation of the implant's braids and the channels in them provide a pathway between the bone marrow at the base of the defect and the overlying bone and cartilage, and may also allow a wicking effect to draw cells and nutrients up through the implant. The orientation of the fibers provides a template for the tissue that is laid down as the wound heals. These columns also intentionally mimic the columnar structure of articular cartilage.

A structure comprised of braids substantially oriented in one direction, such as that shown in FIG. 1A, possesses significant strength and stiffness in that direction. Therefore the implant can be wrapped around an injured tendon or ligament to augment its physical properties and thus aid the healing process.

Any biocompatible polymer that can be fabricated into a fiber could be used to make an implant. Preferred polymers are those that are resorbable. Particularly preferred fibers comprise polymers and copolymers made from glycolic acid, lactic acid, p-dioxanone, 3- and 4-hydroxybutyrates, trimethylene carbonate, and caprolactone. Preferably the polymer is resorbable, and most preferably will be substantially resorbed within a 6 to 18 month timeframe. In a particularly preferred embodiment, the monofilament fibers are resorbable, and degrade in vivo in 6-12 months.

Preferred polymers are those that have a history of safe usage in medical devices such as sutures, including polymers and copolymers of lactic acid, glycolic acid, p-dioxanone, trimethylene carbonate, caprolactone, and hydroxybutyrates, as well as natural or recombinant materials such as silk, and collagen. Derivatized hyaluronic acid polymers such as the Hyaff® materials can also be used. Blends of polymers may also be used to prepare the implants. Non-resorbable polymers could also be used but it is preferable that resorbable materials are used so that a complete biological repair can be achieved.

In a particularly preferred embodiment, poly-4-hydroxybutyrate (P4HB) is used to make the implant. Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, TephaFLEX® biomaterial) is a strong, pliable thermoplastic polyester that, despite its biosynthetic route, has a relatively simple structure.

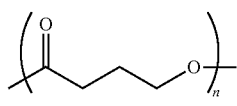

Chemical structure of P4HB

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, biodegradability and relative ease of production.

Chemical synthesis of P4HB has been attempted, but it has been impossible to produce the polymer with a sufficiently high molecular weight that is necessary for most applications (see Hori, Y., et al., *Polymer* 36:4703-4705 (1995); Houk, K. N., et al., *J. Org. Chem.,* 2008, 73 (7), 2674-2678; and Moore, T., et al., *Biomaterials* 26:3771-3782 (2005); Moore, T., et al., *Biomaterials* 26:3771-3782 (2005)).

U.S. Pat. Nos. 6,245,537, 6,623,748, 7,244,442 and 7,906,135 describe methods of making PHAs with little to no endotoxin, which are suitable for medical applications. U.S. Pat. Nos. 6,548,569, 6,838,493, 6,867,247, 7,268,205, 7,179,883, 7,943,683, WO 09/085,823 to Ho et al., and WO 11/159,784 to Cahil et al. describe the use of PHAs to make medical devices. Copolymers of P4HB including 4-hydroxybutyrate copolymerized with 3-hydroxybutyrate or glycolic acid are described in U.S. Pat. No. 8,039,237 by Martin and Skraly, U.S. Pat. No. 6,316,262 to Huisman et al., and U.S. Pat. No. 6,323,010 to Skraly et al. Methods to control the molecular weight of PHA polymers produced by biosynthetic methods have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering. U.S. Pat. No. 8,034,270 discloses medical textiles made from P4HB fibers, including braids. U.S. Pat. No. 8,016,883 discloses devices for ligament and tendon repair made from P4HB meshes. U.S. Pat. No. 7,641,825 discloses fibers of P4HB. U.S. Pat. No. 7,268,205 discloses PHA devices for tendon and cartilage repair comprising P4HB, and U.S. Pat. No. 7,025,980 discloses injectable PHA formulations for soft tissue repair at the knee.

A particularly preferred fiber is a P4HB monofilament fiber with the following properties: diameters ranging from 50 µm to 300 µm, elongation to break of 20-90%, and tensile modulus ranging from 0.1 GPa to 2.0 GPa.

In is a further embodiment, a thin resorbable polymer film can be laminated to the outside of the structure to further facilitate the healing process by reducing or eliminating tissue adhesions.

B. Additional Therapeutic, Prophylactic and/or Diagnostic Agent

1. Ceramic Coatings

To further help the healing process, the braids can be either coated or impregnated with a ceramic. For example, the braids can be coated with calcium phosphate either from a suspension or by precipitating in situ onto the fibers. In a preferred embodiment, the coating is equivalent to between 0.05 to 50% of the polymer fiber weight, and more preferably between 0.05 to 5 wt %. Resorbable bioceramics that can be used in the processes described herein must be: (i) biocompatible, (ii) eventually be resorbed by the body, and (iii) permit the replacement or repair of damaged tissues in the body. Examples of resorbable bioceramics include tricalcium phosphate (α and β forms of TCP—with a nominal composition of $Ca_3(PO_4)_2$), calcium sulfate, calcium carbonate, and other calcium phosphate salt-based bioceramics. Bio-active glasses may also be used. Bioactive glasses are composed of $SiO_2$, $Na_2O$, $CaO$ and $P_2O_5$ in specific proportions.

2. Bioactive Agents

The implant is also compatible with other autologous biological materials such as platelet rich plasma (PRP) and bone marrow aspirate. These materials can be injected into the implant prior to implantation.

In another variant, the braids are also impregnated with hyaluronic acid. This serves the purpose of facilitating clot formation, and/or the healing process. A hyaluronic acid or carboxy methyl cellulose gel may also be used as a carrier for the ceramic impregnation.

Other bioactive agents can be coated onto the implant at the time of manufacture, incorporated in a hyaluronic acid or other polymer coating, or added to the device at the time of implantation. Such bioactive agents include morphogenic proteins and bisphosphonates or other molecule known to positively influence healing.

Diagnostic agents include radiopaque materials, imaging agents, dyes, and magnetic imaging particles.

II. Methods of Manufacturing Implants

A. Polymer Fiber

In a preferred method, fibers are selected and then braided. The braids are subsequently knitted to form a fabric mat that can optionally be coated with a ceramic and other active agents, and then rolled up to form a cylindrical implant. The resulting cylindrical implants comprise a bundle of braids with the axis of the braids substantially parallel to the axis of the bundle so as to provide channels along the axis of the bundle.

In a preferred embodiment, braids are made from monofilament fibers with diameters ranging from 10 µm to 2 mm. In a particularly preferred embodiment, the fibers have diameters ranging from 50 µm to 500 µm, an elongation to break in the range of 0.5% to 1,000%, and a tensile modulus ranging from 0.01 GPa to 10 GPa. In a particularly preferred embodiment, the monofilament fibers are resorbable, and degrade in vivo in 6-12 months.

A particularly preferred fiber is a P4HB monofilament fiber with the following properties: diameters ranging from 50 µm to 300 µm, elongation to break of 20-90%, and tensile modulus ranging from 0.1 GPa to 2.0 GPa.

B. Braids

In a preferred embodiment, the polymer fibers are subsequently braided. The diameters of the braids may be varied depending upon the application, however, braids that are particularly preferred have diameters between 0.1 mm to 2 mm, and more preferably from 0.5 to 1.5 mm. Braids with a diameter of approximately 1.0 mm are particularly preferred for use in osteochondral implants. A particularly preferred braid is made from P4HB monofilament, and is a 4 to 24 carrier braid with between 5 and 70 ppi (picks per inch), and more preferably is a 16 carrier braid with 20 ppi. The braids may further comprise hollow cores or cores that are filled with unbraided fibers or tubes. The use of unbraided fibers in the core will increase the stiffness of the braid, and hence the implant.

The braids or fibers may be assembled substantially in parallel in any manner that provides integrity to the finished device. In a preferred embodiment, the braids (or fibers) are knitted using a weft insertion knitting machine. The fabric mat may be knit to any desired width, but a particularly preferred dimension is approximately 25 mm wide. The distance between the braids can be regular or irregular. In a particularly preferred mat fabric, the braids are spaced at regular intervals every 1.5 mm. The number of warp knits securing the braids may be varied. A preferred number of warp knits is 6 when the width of the mat is 25 mm. Different warp fibers may be used to secure the braids. A particularly preferred choice is a 120 denier 2 dpf multifilament P4HB fiber.

The knitted mat fabrics may be cut to size, and rolled into cylinders to form the implants. The width of the cut depends on the depth of the implant for an osteochondral repair, or on the desired length of coverage for a tendon and ligament reinforcement. In a preferred embodiment for osteochondral implantation, the mat is cut into pieces 1.5 cm wide and 35 mm long which rolls up to form a cylinder implant of approximately 7 mm in diameter and 1.5 cm tall.

Alternative textile forming processes such as 3-D knitting may also be used to prepare suitable structures.

C. Coating with Ceramics and Other Agents

If desired, the final implant or an intermediate in its formation may be coated with a ceramic or other bioactive agent.

The implant may be coated with ceramic by utilization of a number of processes well known in the art. Simulated body fluid (SBF) solutions have been shown to induce apatitic calcium phosphate formation on metals, ceramics, or polymers (with proper surface treatments) soaked in them. This process is very slow. The use of ten-fold increased concentrations have, however, been shown by Tas et al. ("Rapid Coating of Ti6Al4V at room temperature with calcium phosphate solutions similar to 10× simulated body fluid", J. Mater. Res., 19(9), September 2004) to be capable of forming precipitates in a much shorter time. This method has been adapted for coating the fabric mats.

In a preferred embodiment, the ceramic coating is achieved by precipitation from a super physiologic salt solution. In a preferred embodiment the coating is equivalent to 0.05 to 50% of the polymer fiber weight. In a particularly preferred embodiment the coating weight is 0.05% to 5.0% of the fiber weight The proximal 3 mm of the braids of the implant can be masked to prevent them from being impregnated with ceramic, and to thus provide a "cartilage" region to the implant if desired.

A number of other bioactive agents may also be added to the implant (or during the preparation of the implant). Such agents may also be incorporated in controlled release forms. The implant may also be seeded with cells to improve tissue ingrowth and healing.

Wetting agents can also be added to the implant surfaces in order to allow fluids to easily be adsorbed onto the implant surfaces, or to promote cell attachment.

D. Other Methods of Manufacturing Implants

The implants may also be manufactured by drilling holes in suitable matrices to form channels between the upper surface and lower surface of the implant. The implants may also be formed by extruding a multi lumen rod, molding, or using stereolithography to form an implant with channels between the upper and lower surface of the implant. Alternatively a corrugated sheet of material, i.e. a sheet with furrows or ridges, may be rolled up to form a cylindrical implant. These implants may be formed from the materials disclosed herein, and the channels therein may be coated with bioceramics and bioactive agents.

III. Methods of Implanting Implants

As shown in FIG. 2, the tubular osteochondral implants 20 may be delivered through an inserter 30 that is tubular and introduced into a pre-drilled channel 32 that is perpendicular to the articular cartilage. The pre-drilled channel should be sufficiently deep to reach through the diseased and sclerotic bone tissue in order for the regenerating tissue to obtain nutrition from the bone marrow deep below the cartilage surface. In order to minimize thermal necrosis of the wound margins, the holes should preferably be drilled with a sharp and well irrigated drill. The implant is compressed to fit into the inserter, and on removal of the inserter the implant recovers to provide a good fit into the defect.

Prior to implantation, the implant may be soaked or injected in other agents, such as autologous biological materials like platelet rich plasma (PRP) and bone marrow aspirate.

Implants that have been designed to reinforce tendons and ligaments may be implanted by wrapping the implant around an injured tendon or ligament, and securing the device by any suitable means including the use of surgical sutures and glues, or by welding the mat fabric together.

It may also be of value to use the implant in non-hyaline cartilage bone lesions where there is sclerotic or damaged bone. One example is in avascular necrosis of the hip. A hole drilled from the femur into the femoral head can be drilled through the diseased bone and an implant placed to promote healing and regeneration of healthy bone.

The present invention will be further understood by reference to the following non-limiting examples.

Example 1: Manufacture of Knitted Braid Mat

P4HB (Mw 350 kDa) was melt spun and drawn to produce a monofilament fiber 0.13-0.18 mm in diameter with a tensile strength of 1.8 kg and break elongation of 30%. Sixteen spools of the monofilament were then braided to form a 20 ppi braid that was approximately 1 mm in diameter. The braid was then knitted using a weft insertion knitting machine with a 2 dpf, 120 denier multifilament P4HB warp fiber with an average strength of 6 gm/denier and break elongation of 30% to make a 25 mm wide mat with the braids evenly spaced. There were 6 warp knits, and 20 weft insertions per inch.

The mat was then cut into pieces 1 cm wide and 35 mm long. These were then rolled to form a cylindrical implant approximately 7 mm in diameter and 1 cm tall.

Example 2: Ceramic Coating of the Implant

A solution preparation formula (for a total aqueous volume of 1 L) is given in Table 1 for preparing implants with ceramic coatings. The first five chemicals given in Table 1 were added, in the order written, to 950 ml of de-ionized water in a glass beaker of 2 L capacity. Before the addition of the next chemical, the previous one was completely dissolved. After all the reagents were dissolved at room temperature, the solution was made up to 1 L by adding additional water and then filtered with a Nalgene MF75 (90 mm) filter unit for sterilization. This stable sterile stock solution of pH value of 4.35-4.40 could be stored at room temperature in a capped bottle for several months without precipitation.

TABLE 1

Stock solution preparation recipe, for a total volume of 1 L

| Reagent | Order | Amount (g) | Concentration (mM) | Supplier, Cat # & Lot# |
|---|---|---|---|---|
| NaCl | 1 | 58.4430 | 1000 | EMD; 7710; 0613B62 |
| KCl | 2 | 0.3728 | 5 | Mallinckrodt; 6838; 6838Y21610 |
| $CaCl_2 \cdot 2H_2O$ | 3 | 3.6754 | 25 | EMD; CX0134-1; K92681900 |
| $MgCl_2 \cdot 6H_2O$ | 4 | 1.0165 | 5 | Alfa Aesar; 12288; L28U004 |
| $NaH_2PO_4 \cdot 2H_2O$ | 5 | 1.5599 | 10 | J. T. Baker; 3819-01; N04150 |
| $NaHCO_3$ | | | 10 | VWR; BDH0280-500G; 90877 |

Uncoated mats cut to the required size prepared according to Example 1 were washed with 350 mL ethanol (70%) in a media bottle using a shaker (Thermo Scientific*MaxQ 5000) set at 250 rpm for 2 mins. The devices were then left in the hood to air-dry overnight. The weight of each air-dried mat was measured and recorded. A typical mat weighed 200 mg.

Just prior to coating, a 400-ml portion of the stock solution was placed into a 500-ml capacity glass beaker, and an amount (in case of 400 mL stock solution, 1.30 g is added) of $NaHCO_3$ powder was added to raise the hydrogen carbonate ion ($HCO3^-$) concentration to 10 mM, under vigorous stirring. Following the rapid dissolution of the $NaHCO_3$, the pH of the clear solution was monitored with a pH meter (Orion 420) and rose from 4.13 to 6.50 at room temperature. This solution (with an ionic strength of 1137.5 mM) was then transferred to 50 mL centrifuge tubes. Each tube contained one loosely coiled mat and 30 ml of solution. The tube was tightly capped and kept at room temperature for 1 hour. During this time calcium phosphate precipitated onto the surface of the mat.

After one hour the coated device was taken out of the container and rinsed briefly with distilled water (2-3 s) and then with a mini vortexer (VWR) using 20 mL ethanol (70%) for 30 s to remove any of the calcium phosphate coating that was not well bonded to the fiber.

The coated devices were left in a hood to air-dry overnight and then the weight of each coated device was measured and recorded to calculate the coating amount (wt %) of each device. The average coating weight was 0.19% (w/w) with a range of 0.17-0.22% (w/w) for the ten devices coated. Samples were examined using a Scanning Electron Microscope (SEM) and this showed an even coating over all of the fiber.

The coated devices were rolled into a cylinder and placed into the introducer, and then into a pouch. The devices were sterilized using ethylene oxide.

Example 3: Implantation Study

Materials and Methods

A total of six (6) adult goats were enrolled into a study. Two full thickness osteochondral defects, 7.0 mm in diameter by 10.0 mm deep, were created in the middle lateral trochlear sulcus and in the medial femoral condyle of one stifle of each goat. The medial femoral condyle site was exposed to full weight bearing following cast removal while the middle trochlear sulcus will be a protected, limited loaded site. The devices implanted were either ceramic coated or non-coated, and were prepared according to Examples 1 and 2 above. Three goats had ceramic coated implants and three goats had non-coated implants. At the time of implantation blood immediately wicked up into the implants demonstrating the effectiveness of the design. Postoperatively for all animals, the operated rear limb was placed into a modified-Thomas splint for 14 days.

On day 84 (12 weeks) after surgery, animals were humanely euthanized. The left and right femora from each animal was sent for Magnetic Resonance imaging (MRI) of the specimens. The implanted joints were then grossly evaluated for specific changes relative to the treated osteochondral defects.

Results

The right femur with the treated osteochondral defects was sent for histology preparation and analysis.

Evaluation of the MRI images showed that the implants were well integrated into the surrounding tissues and that there were no signs of edema. Gross examination of the joints showed them to be very healthy with no difference in signs of degeneration between the treated and untreated joints. The cartilage was showing signs of repair, even at such an early time after injury.

I claim:

1. A resorbable polymeric textile implantable device for osteo and osteochondral or connective tissue repair comprising braids and a bundle of monofilament fibers, with an axis of monofilament fibers in the bundle substantially parallel to an axis of the device,
wherein the monofilament fibers have a diameter ranging from 50 µm to 500 µm, wherein the device comprises a series of channels communicating between the upper and lower surface of the device which are effective to allow passage of cells and nutrients through the device,
wherein the bundle comprises spaces between the monofilament fibers and
wherein the device is cylindrical.

2. The device of claim 1, wherein the device is porous, and wherein porosity of the device ranges from between 25 and 70%.

3. The device of claim 1, wherein monofilament fibers secure the braids.

4. The device of claim 3 wherein fibers comprise poly-4-hydroxybutyrate (P4HB) or a copolymer thereof.

5. The device of claim 3 wherein the braids have diameters ranging from 0.1 mm to 2 mm.

6. The device of claim 3, wherein the fibers are made from a resorbable polymer or copolymer comprising lactic acid, glycolic acid, p-dioxanone, trimethylene carbonate, caprolactone, hydroxybutyrate, silk, collagen, derivatized hyaluronic acid polymer, polyurethane, polyester or polyanhydride.

7. The device of claim 3, wherein the braids comprise fibers with diameters ranging from 10 μm to 2 mm.

8. The device of claim 7, wherein the braids are knitted, or woven.

9. The device of claim 7, comprising fibers formed from a resorbable polymer or copolymer comprising lactic acid, glycolic acid, p-dioxanone, trimethylene carbonate, caprolactone, and hydroxybutyrates, including 3-hydroxybutyrate and 4-hydroxybutyrate.

10. The device of claim 7, comprising fibers from a resorbable polymer selected from the group consisting of natural or recombinant materials such as silk and collagen, derivatized hyaluronic acid polymers, polyurethanes, polyesters, and polyanhydrides.

11. The device of claim 7 wherein the fibers are coated with a bioactive agent.

12. The device of claim 11 wherein the bioactive agent is a morphogenic protein or a bisphosphonate.

13. The device of claim 1, where the cylinder has a diameter of between 1 and 20 mm.

14. The device of claim 1 wherein the polymeric textile is coated with a bioceramic.

15. The device of claim 14 wherein the bioceramic is α-tricalcium phosphate (TCP), β-TCP, a combination of α- and β-TCP, calcium sulfate, calcium carbonate, or a calcium phosphate salt-based bioceramic.

16. The device of claim 14 wherein a region of the device or channels is not coated with bioceramic.

17. The device of claim 1 wherein a polymer gel is impregnated into the device.

18. The device of claim 17 wherein the polymer gel is comprised of hyaluronic acid or carboxymethylcellulose or contains a particulate bioceramic.

19. The device of claim 18 wherein the bioceramic is α-TCP, β-TCP, a combination of α- and β-TCP, calcium sulfate, calcium carbonate, or a calcium phosphate salt-based bioceramic.

20. The device of claim 1 wherein a bioactive agent is added to the device immediately prior to implantation in the patient.

21. The device of claim 20 wherein the bioactive agent is autologous bone marrow aspirate or platelet rich plasma.

22. The device of claim 1 wherein the device is in the form of a structure that is rolled up to form the device.

23. The device of claim 22 wherein the structure is a sheet, textile, or foam.

24. The device of claim 23 wherein the structure is corrugated.

25. The device of claim 23 wherein the braids comprise poly-4-hydroxybutyrate.

26. The device of claim 1 wherein the device is for the treatment of osteo or osteochondral defects.

27. The device of claim 1 for ligament or tendon repair.

28. The device of claim 27 for ligament and tendon repair, wherein the device comprises a series of fibers or braids formed into a structure with the fibers or braids aligned substantially parallel to each other to form a mat.

29. The device of claim 28 wherein the mat is laminated to a resorbable film.

30. The device of claim 1, wherein the device is compressible to fit into an inserter.

31. A method of making the device of claim 25 comprising the steps of preparing a mat comprising braids and a bundle of monofilament fibers of poly-4-hydroxybutyrate by weft insertion knitting of a braid, with an axis of monofilament fibers in the bundle substantially parallel to an axis of the device,
wherein the monofilament fibers have a diameter ranging from 501 μm to 500 μm,
cutting a strip of the mat that is the width of the desired height of the device, and rolling the mat into a cylinder,
wherein the device comprises a series of channels communicating between the upper and lower surface of the device which are effective to allow passage of cells and nutrients through the device,
wherein the bundle comprises spaces between the monofilament fibers.

32. The method of claim 31 further comprising the step of coating the device with a bioceramic by precipitation from simulated body fluid.

33. A method of using the device of claim 1 wherein the device is inserted into an osteo or osteochondral defect.

34. The method of claim 33 wherein the device is inserted into a surgically created defect.

35. A method of treating a torn ligament or tendon wherein the device of claim 27 is wrapped around the tendon such that the fibers and braids are aligned substantially parallel to the ligament or tendon, and the device is sutured in place.

* * * * *